(12) United States Patent
Waddell

(10) Patent No.: US 10,383,970 B2
(45) Date of Patent: Aug. 20, 2019

(54) ION GENERATOR MOUNTING DEVICE

(71) Applicant: Global Plasma Solutions, LLC, Savannah, GA (US)

(72) Inventor: Charles Houston Waddell, Roanoke, VA (US)

(73) Assignee: Global Plasma Solutions, Inc., Savannah, GA (US)

(*) Notice: Subject to any disclaimer, the term of this patent is extended or adjusted under 35 U.S.C. 154(b) by 0 days.

(21) Appl. No.: 15/896,395

(22) Filed: Feb. 14, 2018

(65) Prior Publication Data

US 2018/0169290 A1    Jun. 21, 2018

Related U.S. Application Data

(63) Continuation of application No. 15/268,717, filed on Sep. 19, 2016, now Pat. No. 9,925,292, which is a (Continued)

(51) Int. Cl.
*H01T 23/00* (2006.01)
*A61L 9/22* (2006.01)
(Continued)

(52) U.S. Cl.
CPC ............ *A61L 9/22* (2013.01); *B01D 46/0032* (2013.01); *B01D 46/521* (2013.01); *B03C 3/011* (2013.01); *B03C 3/04* (2013.01); *B03C 3/155* (2013.01); *B03C 3/41* (2013.01); *B03C 3/82* (2013.01); *F01N 3/0892* (2013.01); *F02M 27/04* (2013.01); *F02M 27/042* (2013.01); *F02M 35/0205* (2013.01); *F02M 35/0217* (2013.01); *F16M 13/02* (2013.01); *F24F 3/166* (2013.01);
(Continued)

(58) Field of Classification Search
None
See application file for complete search history.

(56) References Cited

U.S. PATENT DOCUMENTS 3,744,216 A    7/1973  Halloran
3,804,942 A    4/1974  Kato et al.
(Continued)

FOREIGN PATENT DOCUMENTS

JP    2005-142131 A    6/2005

OTHER PUBLICATIONS http://atmosair.wordpress.com/category/bi-polar-ionization; Oct. 28, 2010; 6 pgs.
(Continued)

*Primary Examiner* — Stephen W Jackson
(74) *Attorney, Agent, or Firm* — Seth L. Hudson; Clements Bernard Walker PLLC

(57) ABSTRACT

The present invention provides methods and systems for an ion generator mounting device for application of bipolar ionization to airflow within a conduit, the device includes a housing for mounting to the conduit having an internal panel within the enclosure, and an arm extending from the housing for extension into the conduit and containing at least one opening. At least one coupling for mounting an ion generator to the arm oriented with an axis extending between a pair of electrodes of the ion generator being generally perpendicular to a flow direction of the airflow within the conduit.

19 Claims, 4 Drawing Sheets

Related U.S. Application Data continuation of application No. 14/861,469, filed on Sep. 22, 2015, now Pat. No. 9,478,948, which is a continuation of application No. 14/480,164, filed on Sep. 8, 2014, now Pat. No. 9,168,538, which is a continuation of application No. 14/036,173, filed on Sep. 25, 2013, now Pat. No. 8,873,215, which is a continuation-in-part of application No. 12/578,753, filed on Oct. 14, 2009, now Pat. No. 8,564,924.

(60) Provisional application No. 61/105,110, filed on Oct. 14, 2008, provisional application No. 61/221,763, filed on Jun. 30, 2009.

(51) Int. Cl.
| | |
|---|---|
| *B03C 3/011* | (2006.01) |
| *B03C 3/41* | (2006.01) |
| *F02M 27/04* | (2006.01) |
| *F16M 13/02* | (2006.01) |
| *H01J 37/16* | (2006.01) |
| *H01J 37/30* | (2006.01) |
| *H01J 27/02* | (2006.01) |
| *F01N 3/08* | (2006.01) |
| *F02M 35/02* | (2006.01) |
| *F24F 3/16* | (2006.01) |
| *B03C 3/04* | (2006.01) |
| *B03C 3/82* | (2006.01) |
| *H01J 37/08* | (2006.01) |
| *B01D 46/00* | (2006.01) |
| *B01D 46/52* | (2006.01) |
| *B03C 3/155* | (2006.01) |

(52) U.S. Cl.
CPC .......... *H01J 27/022* (2013.01); *H01J 27/028* (2013.01); *H01J 37/08* (2013.01); *H01J 37/16* (2013.01); *H01J 37/3002* (2013.01); *H01T 23/00* (2013.01); *A61L 2209/16* (2013.01); *F24F 2003/1682* (2013.01)

(56) References Cited

U.S. PATENT DOCUMENTS

| | | |
|---|---|---|
| 3,956,458 A | 5/1976 | Anderson |
| 4,048,667 A | 9/1977 | Brennecke |
| 4,048,668 A | 9/1977 | Von Bargen et al. |
| 4,244,710 A | 1/1981 | Burger |
| 4,308,844 A | 1/1982 | Persinger |
| 4,417,966 A | 11/1983 | Krauss et al. |
| 4,454,621 A | 6/1984 | Testone |
| 4,519,357 A | 5/1985 | McAllister |
| 4,538,582 A | 9/1985 | Vvakuta |
| 4,597,781 A | 7/1986 | Spector |
| 4,757,422 A | 7/1988 | Bossard et al. |
| 4,809,127 A | 2/1989 | Steinman et al. |
| 4,828,586 A | 5/1989 | Joannou |
| 4,886,526 A | 12/1989 | Joannou |
| 4,901,194 A | 2/1990 | Steinman et al. |
| 4,951,172 A | 8/1990 | Steinman et al. |
| 5,010,869 A | 4/1991 | Lee |
| 5,055,115 A | 10/1991 | Yikai et al. |
| 5,055,963 A | 10/1991 | Partridge |
| 5,108,470 A | 4/1992 | Pick |
| 5,141,529 A | 8/1992 | Oakley et al. |
| 5,185,015 A | 2/1993 | Searle |
| 5,474,599 A | 12/1995 | Cheney et al. |
| 5,486,410 A | 1/1996 | Groeger et al. |
| 5,487,874 A | 1/1996 | Gibboney, Jr. |
| 5,550,703 A | 8/1996 | Beyer et al. |
| 5,573,577 A | 11/1996 | Joannou |
| 5,616,172 A | 4/1997 | Tuckerman et al. |
| 5,656,063 A | 8/1997 | Hsu |
| 5,671,374 A | 10/1997 | Von Glehn |
| 5,702,507 A | 12/1997 | Wang |
| 5,707,429 A | 1/1998 | Lewis |
| 5,741,352 A | 4/1998 | Ford et al. |
| 5,807,425 A | 9/1998 | Gibbs |
| 5,837,207 A | 11/1998 | Summers |
| 5,846,302 A | 12/1998 | Putro |
| 5,950,424 A | 9/1999 | Nojima |
| 5,977,716 A | 11/1999 | Motouchi |
| 6,002,573 A | 12/1999 | Partridge |
| 6,036,738 A | 3/2000 | Shanbrom |
| 6,053,968 A | 4/2000 | Miller |
| 6,058,698 A | 5/2000 | Coral et al. |
| 6,063,167 A | 5/2000 | Rutkowski |
| 6,090,184 A | 7/2000 | Cartellone |
| 6,118,645 A | 9/2000 | Partridge |
| 6,149,717 A | 11/2000 | Satyapal et al. |
| 6,322,614 B1 | 11/2001 | Tillmans |
| 6,463,917 B1 | 10/2002 | Silver |
| 6,471,752 B1 | 10/2002 | Lewis |
| 6,536,418 B1 | 3/2003 | Ling |
| 6,601,570 B2 | 8/2003 | Zetmeir |
| 6,610,123 B2 | 8/2003 | Wu et al. |
| 6,693,788 B1 | 2/2004 | Partridge |
| 6,752,970 B2 | 6/2004 | Schwartz et al. |
| 6,764,533 B2 | 7/2004 | Lobiondo, Jr. |
| 6,785,114 B2 | 8/2004 | Gorczyca et al. |
| 6,805,732 B1 | 10/2004 | Billiotte et al. |
| 6,807,044 B1 | 10/2004 | Vernitsky et al. |
| 6,850,403 B1 | 2/2005 | Gefter et al. |
| 7,132,010 B2 | 11/2006 | Carlsson |
| 7,177,133 B2 | 2/2007 | Riskin |
| 7,256,979 B2 | 8/2007 | Sekoguchi et al. |
| 7,258,729 B1 | 8/2007 | Barsimanto et al. |
| 7,311,752 B2 | 12/2007 | Tepper et al. |
| 7,341,049 B2 | 3/2008 | Clack |
| 7,347,888 B2 | 3/2008 | Hecker et al. |
| 7,368,003 B2 | 5/2008 | Crasper et al. |
| 7,384,619 B2 | 6/2008 | Bar-Gadda |
| 7,391,598 B2 | 6/2008 | Fujiwara et al. |
| 7,407,624 B2 | 8/2008 | Cumberland et al. |
| 7,475,656 B2 | 1/2009 | Yatsenko |
| 7,497,898 B2 | 3/2009 | Sato et al. |
| 7,691,335 B2 | 4/2010 | Park et al. |
| 7,749,313 B2 | 7/2010 | Byon et al. |
| 7,858,054 B2 | 12/2010 | Manalo |
| 7,906,080 B1 | 3/2011 | Botvinnik |
| 7,948,733 B2 | 5/2011 | Hashimoto |
| 8,018,710 B2 | 9/2011 | Fujita et al. |
| 8,038,775 B2 | 10/2011 | Gefter |
| 8,072,731 B2 | 12/2011 | Shimada et al. |
| 8,106,367 B2 | 1/2012 | Riskin |
| 8,134,821 B2 | 3/2012 | Fukai et al. |
| 8,564,924 B1 | 10/2013 | Waddell et al. |
| 8,873,215 B2 | 10/2014 | Waddell |
| 9,168,538 B2 * | 10/2015 | Waddell .................. H01T 23/00 |
| 2005/0123436 A1 | 6/2005 | Cumberland |
| 2005/0142047 A1 | 6/2005 | Baik et al. |
| 2007/0034082 A1 | 2/2007 | Adair et al. |
| 2008/0098895 A1 | 5/2008 | Sato et al. |
| 2008/0274012 A1 | 11/2008 | Cumberland et al. |
| 2009/0044703 A1 | 2/2009 | Bias et al. |
| 2009/0052108 A1 | 2/2009 | Innami et al. |
| 2009/0103229 A1 | 4/2009 | Jung et al. |
| 2010/0008010 A1 | 1/2010 | Orihara et al. |
| 2010/0018398 A1 | 1/2010 | Krell et al. |
| 2010/0175391 A1 | 7/2010 | Jee et al. |
| 2010/0247389 A1 | 9/2010 | Abate |
| 2010/0251889 A1 | 10/2010 | Haruna et al. |
| 2011/0016700 A1 | 1/2011 | Egley et al. |
| 2012/0154973 A1 | 6/2012 | Vaynerman et al. |
| 2013/0232807 A1 | 9/2013 | Robert et al. |

OTHER PUBLICATIONS

Wide Area Ionizer is the choice for your production site, https://www.panasonic-electric-works.com/cps/rde/xber/penew/ds_63165_1000_en_ertf.pdf, Mar. 2009.

(56) References Cited

OTHER PUBLICATIONS

Series IZS31 Specification Data.
Brochure, Sterionizer Window, Jan. 2009 (trade show).
New Wide Area Ionizer of Flexible Mounting for Cell Production-The Sunx ER-TF Series, http://news.thomasnet.com/fullstory/Static-Ionizer-is-for-use-in-cell-manufacturing-facilities-819753, Aug. 1, 2008.

* cited by examiner

ION GENERATOR MOUNTING DEVICE

CROSS REFERENCE TO RELATED PATENT APPLICATION

This application is a continuation of U.S. patent application Ser. No. 15/268,717 filed on Sep. 19, 2016, which in turn is a continuation of U.S. Pat. No. 9,478,948 granted on Oct. 25, 2016, which in turn is a continuation of U.S. Pat. No. 9,168,538 granted Oct. 27, 2015, which in turn is a continuation of U.S. Pat. No. 8,873,215 issued Oct. 28, 2014, which in turn is a continuation-in-part of U.S. Pat. No. 8,564,924 issued Oct. 22, 2013, which claims the benefit of U.S. Provisional Patent Application Ser. No. 61/105,110 filed Oct. 14, 2008 and U.S. Provisional Patent Application Ser. No. 61/221,763 filed Jun. 30, 2009, the contents of which are incorporated in full by reference herein.

FIELD OF THE INVENTION

The present invention relates generally to the field of air treatment, and more particularly to the treatment of air using ionization, including bipolar ionization.

BACKGROUND OF THE INVENTION

Air and other fluids are commonly treated and delivered for a variety of applications. For example, in heating, ventilation and air-conditioning (HVAC) applications, air may be heated, cooled, humidified, dehumidified, filtered or otherwise treated for delivery into residential, commercial or other spaces.

Needs exist for improved systems and methods for mounting ion generator devices for treating and delivering air for these and other applications. It is to the provision of improved mounting devices for systems and methods meeting these needs that the present invention is primarily directed.

BRIEF SUMMARY OF THE INVENTION

According to an embodiment of the present invention, an ion generator mounting device includes a housing having base, a first and second pair of spaced-apart, opposed sidewalls projecting from the base to collectively form an interior storage compartment and to define an upper edge, a top portion, at least one opening within the housing and a retention means extending outwardly from the housing.

According to another embodiment of the present invention, an ion generator mounting device includes an ion generator disposed within the interior storage compartment.

According to yet another embodiment of the present invention, an ion generator mounting device includes an ion generator containing at least one electrode for dispersing ions from the bipolar ionization generator that is disposed within the interior storage compartment, whereby at least one electrode is disposed adjacent that at least one opening.

According to yet another embodiment of the present invention, an ion generator mounting device includes a power supply.

According to yet another embodiment of the present invention, an ion generator mounting device includes a switch.

According to yet another embodiment of the present invention, an ion generator mounting device includes a retention means disposed on one of the sidewalls and extending therefrom.

According to yet another embodiment of the present invention, an ion generator mounting device includes an LED disposed on the housing.

According to yet another embodiment of the present invention, an ion generator mounting device includes an elongate arm that includes a first side and a second side, whereby the first side contains at least one opening and an ion generator with at least one electrode that is disposed adjacent the second side of the arm, such that the at least one electrode is disposed adjacent the at least one opening.

According to yet another embodiment of the present invention, an ion generator mounting device includes an elongate arm with a top side and a bottom side.

According to yet another embodiment of the present invention, an ion generator mounting device includes mountings that engage an ion generator to the arm.

According to yet another embodiment of the present invention, an ion generator mounting device includes electrodes of the ion generator that are axially aligned with the arm.

According to yet another embodiment of the present invention, an ion generator mounting device includes electrical contacts disposed within the arm.

According to yet another embodiment of the present invention, an ion generator mounting device includes a housing that includes a base, a first and second pair of spaced-apart, opposed sidewalls projecting from the base to collectively form an interior storage compartment and to define an upper edge, a top portion, and a securing means for selectively securing the top portion to the base.

According to yet another embodiment of the present invention, an ion generator mounting device for application of ionization to an airflow within a conduit, the device includes a housing for mounting to the conduit having an internal panel within the enclosure, an arm extending from the housing for extension into the conduit and containing at least one opening, and at least one coupling for mounting an ion generator to the arm oriented with an axis extending between a pair of electrodes of the ion generator being generally perpendicular to a flow direction of the airflow within the conduit.

According to yet another embodiment of the present invention, an ion generator mounting device includes a coupling that comprises electrical contacts on the arm for delivering power to the at least one ion generator.

According to yet another embodiment of the present invention, an ion generator mounting device includes at least one terminal block for wiring connection to the ion generators via contacts on the arm.

According to yet another embodiment of the present invention, an ion generator mounting device includes a power converter for converting input power to operate the ion generators.

According to yet another embodiment of the present invention, an ion generator mounting device that includes at least one electrode that is recessed within an opening on the arm and below the horizontal plane of the external surface of the arm.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The present invention includes a number of ion generator carrier and mounting assemblies for application and control of delivery of ionization to an airflow, including bipolar ionization.

Figure 1A:
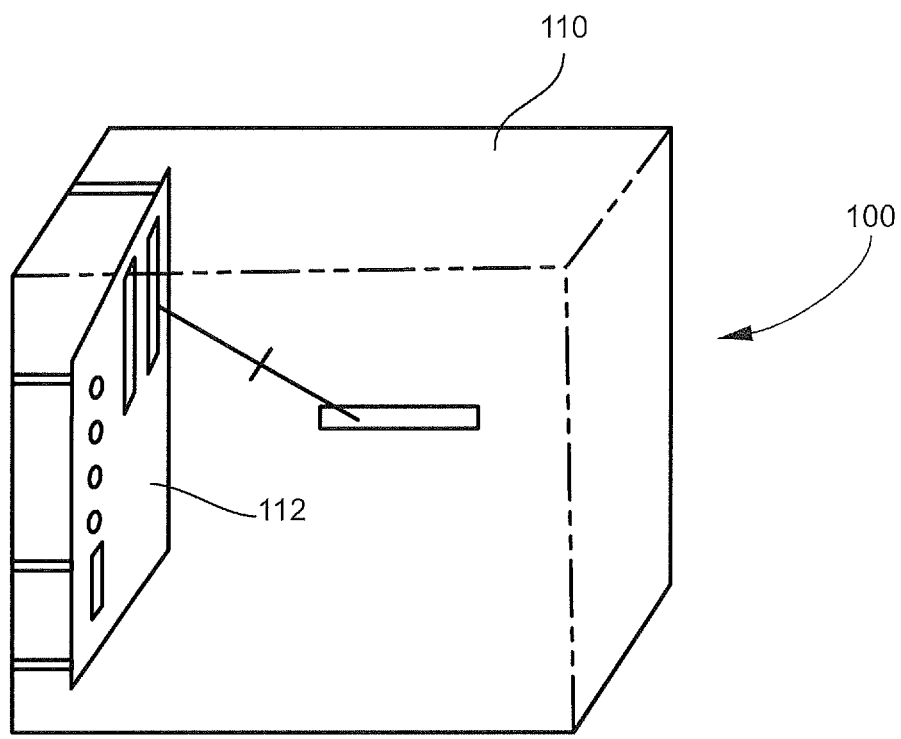
FIG. 1A is a perspective view of an embodiment of the present invention.
Figure 1B:
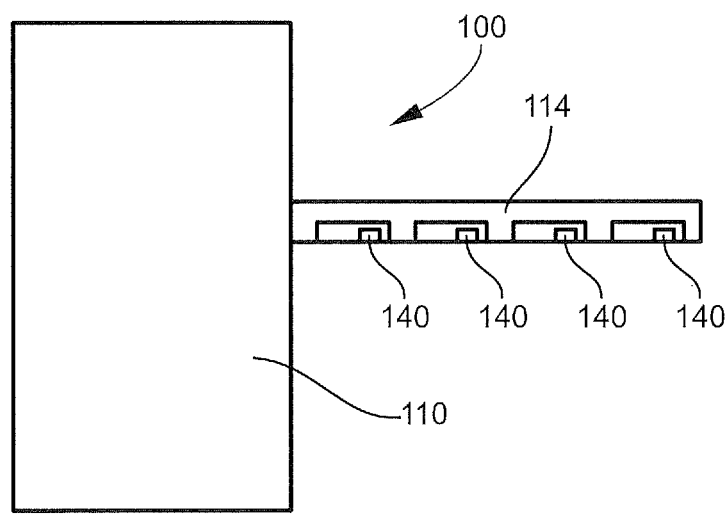
FIG. 1B is a perspective view of an alternative embodiment of the present invention.

FIGS. 1a and 1b show an exemplary embodiment of an assembly 100 for mounting to the exterior of a duct, housing, or other conduit for airflow. The assembly includes a housing 110 or other enclosure, such as for example a NEMA 4x enclosure or similar configuration, an internal panel 112 within the housing 110, and an external arm 114 projecting from the back side of the housing. The external arm 114 includes mountings and electrical contacts for receiving one or more ion generators 140 for delivery of bipolar ionization to airflow within a conduit. Alternatively, the arm 114 may be disposed adjacent a cooling coil. Such ion generator 140 can include the Sterionizer™ device that may be purchased from Filt-Air, a Beth-El Group, Israel, and includes a pair of electrodes that disperse ions. The mountings securely engage the ion generator 140 or ion generators 140 and maintain them in an orientation having their electrodes axially aligned with the arm 114 and generally perpendicular to the airflow. The panel 112 optionally comprises one or more pluggable terminal blocks for wiring connection to the ion generators 140 via the contacts on the arm 114, a connection for power input, and one or more indicators such as light emitting diodes (LEDs) to indicate the presence/absence and operational state (on/off, ion output, etc.) of the ion generators 140. Optionally, a power converter or transformer is provided in the housing 110 for converting the input power to the power required to operate the ion generators 140. One or more connectors are optionally provided for mounting the housing 110 to the exterior of a duct or housing, with the arm 114 extending into the duct or housing through an opening formed therein. Sealing means such as a gasket are optionally provided on the back of the housing 110 around the arm 114 for sealing around the opening.

Figure 2:
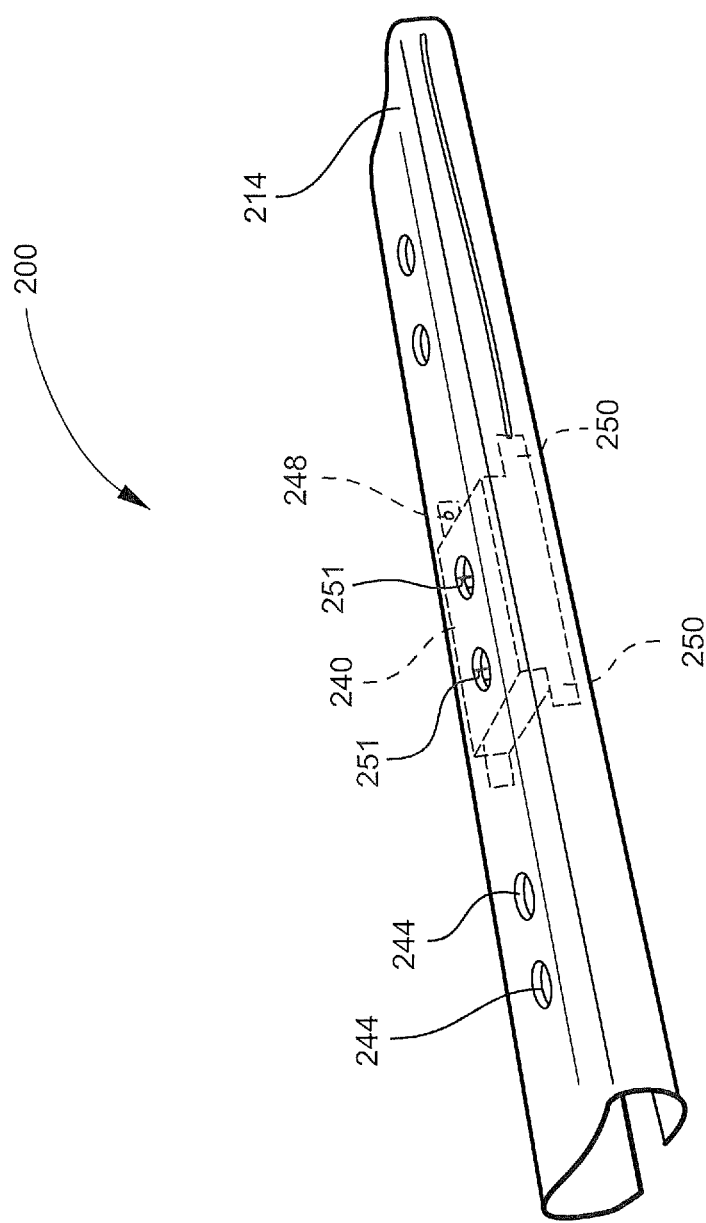
FIG. 2 is a perspective view of an arm of the present invention.
Figure 3:
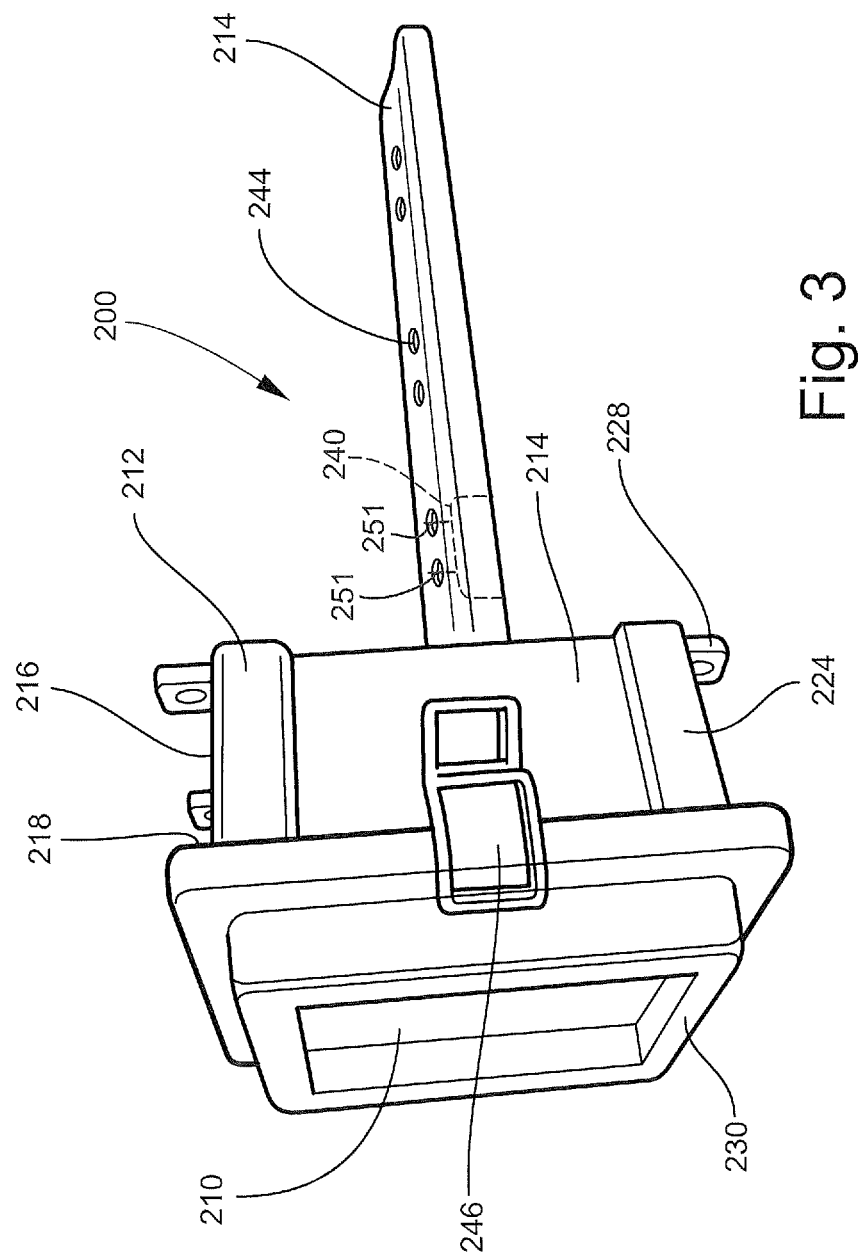
FIG. 3 is a perspective view of an alternative embodiment of the present invention.
Figure 4:
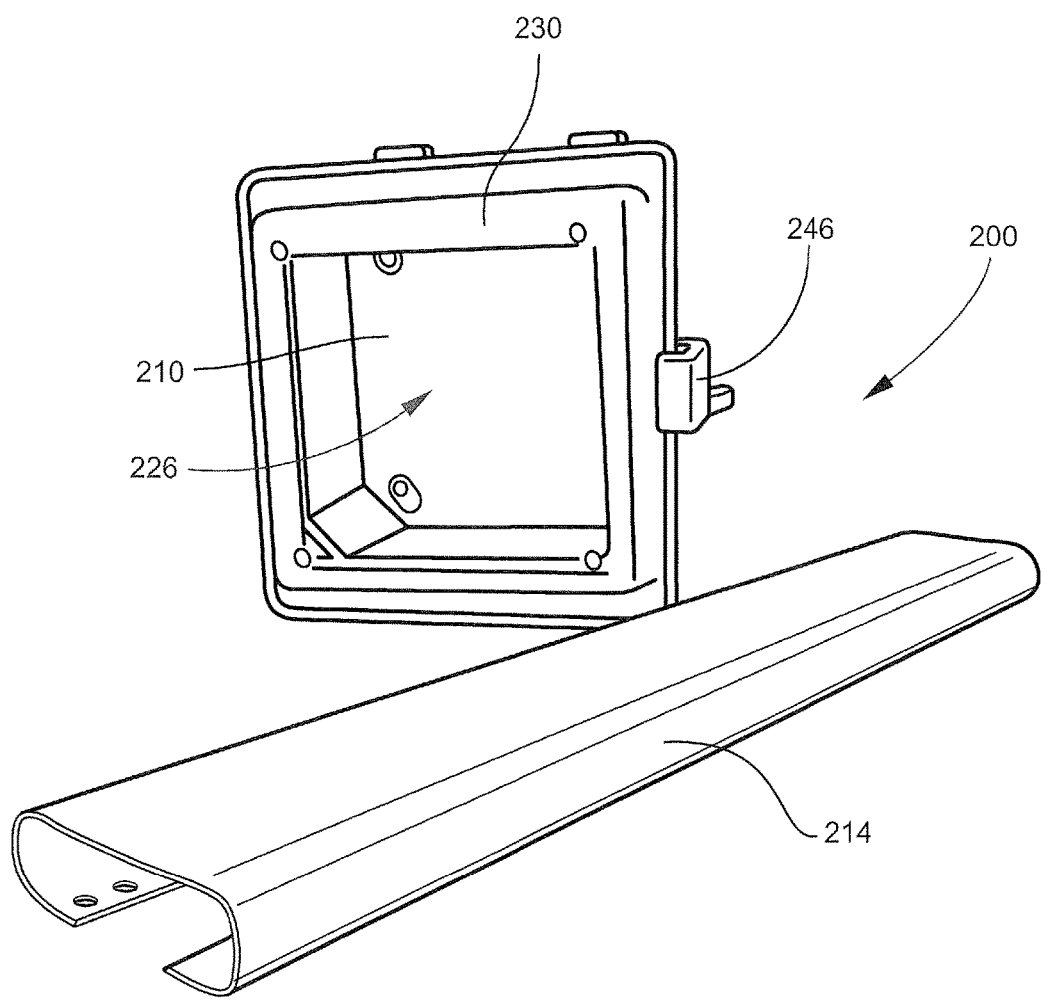
FIG. 4 is another perspective view of an alternative embodiment of the present invention.

FIGS. 2, 3 and 4 show a device 200 according to an alternate embodiment, having a housing 210 with an arm 214 extending therefrom. The length of the arm 214 may vary depending on the size of the conduit it is to be applied to and the number of ion generators to be installed, and in example embodiments is between 2"-24", for example about 10" in length.

The arm 214 is generally elongate and extends outwardly from the housing 210 and has a top side, a bottom side, a first side, and a second side. The arm 214 contains at least one opening 244 contained therein in. The arm 214 includes mountings 248 and electrical contacts 250 for receiving one or more ion generators 240 for delivery of ionization to an airflow within the conduit. Such ion generator can include the Sterionizer™ device that may be purchased from Filt-Air, a Beth-El Group, Israel, and includes a pair of electrodes that disperse ions. The mountings 248 securely engage the ion generators 240 and maintain them in an orientation having their electrodes axially aligned with the arm 214 and generally perpendicular to the airflow. The panel 212 optionally comprises one or more pluggable terminal blocks for wiring connection to the ion generators 220 via the contacts on the arm 214, a connection for power input, and one or more indicators such as LEDs 242 to indicate the presence/absence and operational state (on/off, ion output, etc.) of the ion generators 220. Optionally, a power converter or transformer is provided in the housing 210 for converting the input power to the power required to operate the ion generators 240. One or more connectors are optionally provided for mounting the housing 210 to the exterior of a duct or housing, with the arm 214 extending into the duct or housing through an opening formed therein. Sealing means such as a gasket are optionally provided on the back of the housing 210 around the arm 214 for sealing around the opening.

The electrodes of the ion generators 240 are placed in close proximity to the opening 220 on the arm 214, thus allowing the ions to disperse through the arm 214. The electrodes are recessed within the arm 214. In other words, the electrodes of the ion generators 240 do not break the horizontal plane of the external of the top side of the arm 214 and are located equal to or beneath the horizontal plane of the arm 214 for allowing the ions to disperse through the openings 244 in the arm 214.

As illustrated in FIGS. 2, 3, and 4, the arm 214 contains two openings 244 for each ion generator 220. In another alternative embodiment, the electrodes of the ion generator 220 may protrude through the openings 244 and extend above the horizontal plane of the arm 214. The housing 210 includes a base 212 that extends to an outer edge. First and second pairs of opposed sidewalls 214, 216 extend from the outer edge of the base 212 to an upper edge 218. The sidewalls 214, 216 each have an inner and outer sidewall surfaces 220, 222. Each of the second pair of sidewalls 216 interconnects the first pair of sidewalls 214 to define corners 224 and an interior storage compartment 226. At least one retention member 228 extends from a first or second sidewall 214, 216 or the base 212. A top portion 230 may be selectively secured to the base 212. As illustrated, the top portion 230 is hingedly connected to the first or second sidewall 214, 216 and includes a latch 246 for selectively securing the top portion 230 to the base 212.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. An ion generator mounting device, comprising:
   a housing comprising:
   a base,
   a first and second pair of spaced-apart, opposed sidewalls projecting from the base to collectively form an interior storage compartment and to define an upper edge;
   a top portion hingedly connected to at least one sidewall;
   a latch;
   at least one opening within the housing;
   at least one retention member extending outwardly from at least one sidewall; and
   at least one coupling for mounting the ion generator.

2. The ion generator mounting device of claim 1, further comprising an ion generator disposed within the interior storage compartment.

3. The ion generator mounting device of claim 1, further comprising an ion generator containing at least one electrode for dispersing ions from the ion generator that is disposed within the interior storage compartment, whereby at least one electrode is disposed adjacent that at least one opening.

4. The ion generator mounting device of claim 1, further comprising a power supply.

5. The ion generator mounting device of claim 1, further comprising a switch.

6. The ion generator mounting device of claim 1, further comprising an indicator disposed on the housing.

7. An ion generator mounting device, comprising:
   an elongate arm, comprising a first side and a second side, the length of the arm is between 2 inches and 24 inches, whereby the first side contains at least one opening and an ion generator with at least one electrode that is disposed adjacent the second side of the arm, such that the at least one electrode is disposed adjacent the at least one opening.

8. The ion generator mounting device of claim 7, further comprising an elongate arm with a top side and a bottom side.

9. The ion generator mounting device of claim 7, further comprising mountings that engage the ion generator to the arm.

10. The ion generator mounting device of claim 7, wherein the electrodes of the ion generator is axially aligned with the arm.

11. The ion generator mounting device of claim 7, further comprising electrical contacts disposed within the arm.

12. The ion generator device of claim 7, further comprising a housing engaged to the arm.

13. The ion generator mounting device of claim 7, further comprising a housing comprising: a base, a first and second pair of spaced-apart, opposed sidewalls projecting from the base to collectively form an interior storage compartment and to define an upper edge; and a top portion, a securing means for selectively securing the top portion to the base.

14. The ion generator mounting device of claim 7, further comprising an LED disposed on the device.

15. An ion generator mounting device for application of bipolar ionization to an airflow within a conduit, the device comprising:
   a housing for mounting to the conduit having an internal panel within the enclosure;
   an arm extending from the housing for extension into the conduit and containing at least one opening, the length of the arm is between 2 inches and 24 inches;
   at least one coupling for mounting an ion generator to the arm oriented with an axis extending between a pair of electrodes of the ion generator being generally perpendicular to a flow direction of the airflow within the conduit; and
   one or more LEDs to indicate the operational state of the ion generator.

16. The ion generator mounting device of claim 15, wherein the coupling comprises electrical contacts on the arm for delivering power to the at least one ion generator.

17. The ion generator mounting device of claim 15, further comprising at least one terminal block for wiring connection to the ion generator via contacts on the arm.

18. The ion generator mounting device of claim 15, further comprising a power converter for converting input power to operate the ion generator.

19. The ion generator mounting device of claim 15, wherein the ion generator contains at least one electrode that is recessed within an opening on the arm and below the horizontal plane of the external surface of the arm.

* * * * *